United States Patent [19]

Merkel et al.

[11] Patent Number: 4,492,710
[45] Date of Patent: Jan. 8, 1985

[54] SUBSTITUTED PYRROLIDINYL-BENZOIC ACID DERIVATIVES AND A PROCESS FOR THEIR MANUFACTURE

[75] Inventors: Wulf Merkel; Dieter Bormann, both of Kelkheim; Roman Muschaweck, Frankfurt am Main, all of Fed. Rep. of Germany

[73] Assignee: Hoechst Aktiengesellschaft, Frankfurt am Main, Fed. Rep. of Germany

[21] Appl. No.: 421,030

[22] Filed: Sep. 22, 1982

Related U.S. Application Data

[63] Continuation of Ser. No. 146,017, May 2, 1980, abandoned.

[30] Foreign Application Priority Data

May 4, 1979 [DE] Fed. Rep. of Germany ..... 29179973

[51] Int. Cl.³ ................. A61K 31/44; A61K 31/40; C07D 207/327; C07D 401/12
[52] U.S. Cl. ..................................... 424/274; 548/569; 548/527; 546/281; 424/263
[58] Field of Search ............. 548/565, 577, 569; 424/274

[56] References Cited

FOREIGN PATENT DOCUMENTS 2718494 11/1978 Fed. Rep. of Germany.
186059 11/1979 New Zealand.
1589339 5/1981 United Kingdom.
1589340 5/1981 United Kingdom.

*Primary Examiner*—Mark L. Berch
*Attorney, Agent, or Firm*—Curtis, Morris & Safford

[57] ABSTRACT

What are disclosed are pyrrolidinylsulfamoylbenzoic acid compounds of the formula

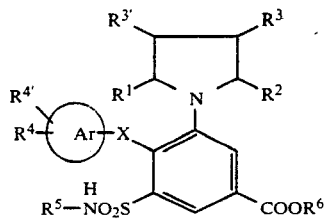

in which $R^1$ and $R^2$ denote $C_1$–$C_4$alkyl and one of the radicals $R^1$ or $R^2$ may be hydrogen, $R^3$ and $R^{3'}$ denote hydrogen or $C_1$–$C_4$alkyl or together denote a C—C linkage, $R^4$ and $R^{4'}$ denote hydrogen, halogen, $CF_3$, alkyl or $C_1$–$C_2$alkoxy, hydroxy, amino or dimethylamino in the various positions of the aryl nucleus, or together denote 3,4-methylenedioxy, $R^5$ and $R^6$ denote hydrogen, $C_1$–$C_4$alkyl or benzyl, Ar denotes phenyl or a 5-membered or 6-membered heteroaromatic ring containing a O, S or N atom and X is omitted or denotes oxygen, sulfur, NH, or $CH_2$, and their pharmaceutically acceptable salts with bases or acids. The compounds and salts have a salidiuretic action and can be used for the treatment of edematous diseases.

7 Claims, No Drawings

SUBSTITUTED PYRROLIDINYL-BENZOIC ACID DERIVATIVES AND A PROCESS FOR THEIR MANUFACTURE

This is a continuation of application Ser. No. 146,017, filed May 2, 1980, now abandoned.

The invention relates to substituted pyrrolidinylsulfamoylbenzoic acid derivatives of the general formula I

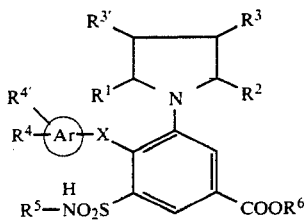

in which $R^1$ and $R^2$ are identical or different and denote alkyl with 1–4 C atoms and one of the radicals $R^1$ or $R^2$ can also be hydrogen, $R^3$ and $R^{3'}$ are identical or different and denote hydrogen or alkyl with 1–4 C atoms, or together denote a C—C double bond, $R^4$ and $R^{4'}$ are identical or different and denote hydrogen, halogen, $CF_3$, alkyl or alkoxy with 1–2 C atoms, hydroxyl, amino or dimethylamino, in the various positions of the aryl nucleus, or together denote the 3,4-methylenedioxy group, $R^5$ and $R^6$ are identical or different and denote hydrogen, alkyl with 1–4 C atoms or benzyl, Ar denotes phenyl or a 5-membered or 6-membered heteroaromatic ring containing a O, S or N atom and X is omitted or denotes oxygen, sulfur, NH or $CH_2$, and to their pharmaceutically acceptable salts with bases or acids.

If X is "omitted", this means that the substituent Ar is bonded directly to the benzoic acid radical and thus forms a biaryl system.

The substituents $R^1$, $R^2$, $R^3$ and $R^{3'}$ on the pyrrolidine ring can be arranged in any of the possible stereoisomeric positions.

The invention also relates to a process for the manufacture of the compounds of the formula I, which comprises reacting 3-aminobenzoic acid derivatives of the general formula II

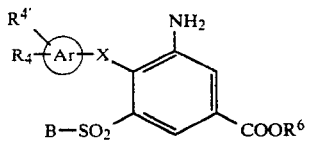

in which $R^4$, $R^{4'}$, $R^5$, $R^6$, X and Ar have the indicated meanings and B denotes either the group $NHR^5$ or the grouping III

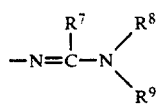

in which the radicals $R^7$, $R^8$ and $R^9$ represent a lower alkyl group but $R^7$ can also be hydrogen and/or any two of the substituents can also be cyclically bonded to one another, with 2,5-dialkoxytetrahydrofurans of the formula IV

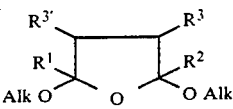

or with 1,4-diketones of the formula V

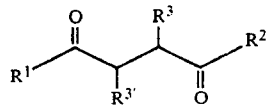

in which $R^1$, $R^2$, $R^3$ and $R^{3'}$ have the indicated meanings and Alk represents lower alkyl with 1–4 C atoms, and reducing the resulting compounds of the formula VI

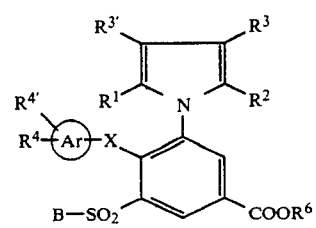

in which the radicals $R^1$–$R^6$ and B have the meaning given above, and optionally hydrolyzing the said compounds, before or after the reduction, and optionally esterifying resulting compounds of the formula VI in which $R^6$=H and/or converting the resulting compounds I into pharmaceutically acceptable salts with acids or bases.

The amino compounds of the formula II which are used as starting materials are known from the literature or can be manufactured by routes analogous to those indicated in the literature. The tetrahydrofurans IV and the diketones V are likewise known from the literature.

If B in formulae II and VI denotes the NHR group and $R^6$ denotes hydrogen, compounds of the formula I in which $R^6$=H are obtained direct by reduction of the compounds of the formula VI.

If $R^6$ does not denote hydrogen and/or B denotes the grouping III, either the compounds of the formula VI are subsequently hydrolyzed and the acids of the general formula VI in which $R^6$=H, which are thus obtained, are catalytically reduced to compounds of the general formula I in which $R^6$=H, or catalytic hydrogenation is first carried out and this is followed by hydrolysis, since the protected sulfamoyl group is not attacked during catalytic hydrogenation.

Pharmaceutically acceptable salts which can be used are, in particular, alkali metal salts and alkaline earth metal salts, such as, for example, Na, K, $NH_4$ or Ca salts, but also salts of organic bases, such as, for example, the ethanolamine salt.

Pharmaceutically acceptable esters which may be mentioned are the lower alkyl esters, for example the methyl, ethyl or isopropyl esters.

The reaction of the amines II with the tetrahydrofurans IV is carried out in a manner which is in itself known, in accordance with Acta Chem. Scand. 6, 867 (1952). It is carried out with the aid of a dilute mineral acid or organic acids, preferably glacial acetic acid. The use of a mixture of a chlorinated solvent, preferably chloroform or methylene chloride, with glacial acetic acid has proved particularly advantageous. The reactions can be carried out at the boiling point of the particular solvent or solvent mixture or also at room temperature.

The reaction of the amines II with the diketones V is likewise carried out in a manner which is in itself known, in accordance with Chem. Ber. 109, 3,426 (1976). It is carried out in weak organic acids, preferably glacial acetic acid, or in a neutral organic solvent, preferably dioxane, in the presence of catalytic amounts of strong mineral acids or organic acids, preferably p-toluenesulfonic acid, in each case at the boiling point.

The reaction of the amines containing a protected sulfamoyl group (B=grouping III) in most cases results in higher yields than are obtained when the amines containing a free sulfamoyl group are used and is therefore to be preferred.

The compounds of the general formula VI which are thus obtained are optionally precipitated by adding water. Preferably, the compounds are now hydrolyzed with alkali metal hydroxides. The compounds of the formula VI ($R^6$=H) can be isolated by subsequently acidifying to pH 2-4.

The reduction of the compounds of the general formula VI, which optionally can also be carried out prior to the hydrolysis, is advantageously effected by catalytic hydrogenation. Catalysts which can be used are the catalysts customary for catalytic hydrogenation, for example Pd/active charcoal, $PtO_2$, Rh/active charcoal or Pt/active charcoal. The hydrogenation reactions are carried out with hydrogen under a pressure of 1-150 atmospheres and preferably under 20-100 atmospheres, and also at room temperature up to 150° C. and advantageously at 60°-100° C. The solvents employed are the solvents customarily used for catalytic hydrogenation reactions, for example organic acids, such as glacial acetic acid, or organic alcohols, ethers or esters, such as, for example, methanol, dioxane or ethyl acetate.

The way in which the reduced compounds are isolated depends on the nature of the solvent and in many cases isolation is effected by precipitating the compounds with a non-solvent, such as, say, water or hydrocarbons such as petroleum ether, or, alternatively, by evaporating off the solvent used.

The reduction can also be carried out with other reducing agents known for pyrroles, such as, for example, glacial acetic acid/zinc or hydroiodic acid and red phosphorus.

If $R^4$ and $R^{4'}$ denote OH, SH and/or $NH_2$ groups, these groups can be protected in compounds of the formula VI, for example by an acyl group or by a benzyl radical. On catalytic hydrogenation or hydrolysis of compounds of the general formula VI, these protective groups are then also detached at the same time.

In addition to the compounds described in the examples, the compounds mentioned below can be prepared: 4-phenoxy-3-(2,5-diethyl-1-pyrrolidinyl)-5-sulfamoyl-benzoic acid, 4-(4-fluorophenoxy)-3-(2,5-dimethyl-1-pyrrolidinyl)-5-sulfamoyl-benzoic acid, 4-(4-trifluoromethylphenoxy)-3-(2,5-dimethyl-1-pyrrolidinyl)-5-sulfamoyl-benzoic acid, 4-(4-hydroxyphenoxy)-3-(2,5-dimethyl-1-pyrrolidinyl)-5-sulfamoyl-benzoic acid, 4-(4-aminophenoxy)-3-(2-methyl-1-pyrrolidinyl)-5-sulfamoyl-benzoic acid, 4-phenylthio-3-(2,5-dimethyl-1-pyrrolidinyl)-5-sulfamoyl-benzoic acid, 4-anilino-3-(2,5-dimethyl-1-pyrrolidinyl)-5-sulfamoyl-benzoic acid, 4-(4-methylanilino)-3-(2,5-dimethyl-1-pyrrolidinyl)-5-sulfamoyl-benzoic acid, 4-phenyl-3-(2,5-diethyl-1-pyrrolidinyl)-5-sulfamoyl-benzoic acid, 4-(4-methoxyphenyl)-3-(2,5-dimethyl-1-pyrrolidinyl)-5-sulfamoyl-benzoic acid, 4-(4-methylphenyl)-3-(2,5-dimethyl-1-pyrrolidinyl)-5-sulfamoyl-benzoic acid, 4-(3-thienyl)-3-(2,5-dimethyl-1-pyrrolidinyl)-5-sulfamoyl-benzoic acid, 4-(3,4-methylenedioxyphenoxy)-3-(2,5-dimethyl-1-pyrrolidinyl)-5-sulfamoyl-benzoic acid, 4-(3-dimethylaminophenoxy)-3-(2,5-dimethyl-1-pyrrolidinyl)-5-sulfamoyl-benzoic acid, 4-(3-methylphenoxy)-3-(2-ethyl-1-pyrrolidinyl)-5-sulfamoyl-benzoic acid, 4-(4-methylphenoxy)-3-(2,4-dimethyl-1-pyrrolidinyl)-5-sulfamoyl-benzoic acid, 4-phenoxy-3-(2,3,4-trimethyl-1-pyrrolidinyl)-5-sulfamoyl-benzoic acid, 4-(4-methylphenoxy)-3-(2,3,5-trimethyl-1-pyrrolidinyl)-5-sulfamoyl-benzoic acid, 4-phenoxy-3-(2,3,4,5-tetramethyl-1-pyrrolidinyl)-5-sulfamoyl-benzoic acid and 4-(4-methylphenoxy)-3-(2,3-dimethyl-1-pyrrolidinyl)-5-sulfamoyl-benzoic acid.

The sulfamoylbenzoic acid derivatives, according to the invention, of the formula I and their pharmaceutically acceptable salts are highly active diuretic agents and salidiuretic agents, which can be employed in human medicine and in veterinary medicine. The pyrroles of the general formula VI ($R^6$=H and B=NHR), which have been described as intermediate products, can also be highly active pharmaceuticals, especially diuretic agents and saluretic agents and can be used therapeutically.

The compounds I and VI (B=NHR) are administered in dosages of 0.5 to 100 mg, in capsules, sugar-coated tablets, tablets or solutions with diverse additives, enterally, for example orally using a probang or the like, or parenterally (injection into the vascular system, for example intravenously, or injection into the musculature or under the skin and the like). They are suitable for the treatment of edematous diseases, such as cardiac and renal edemas or edemas caused by hepatitis, and other phenomena which are due to disorders in the water balance and electrolyte metabolism. The compounds can be used on their own or in combination with other substances having a salidiuretic action, including those having a different mode of action, or can be administered with diverse other medicaments, separately, alternately or in combination. Medicaments to be mentioned in particular are spironolactone, triameteren, amiloride and other $K^+$-retaining compounds alternating with long-acting salidiuretic agents of the chlorthalidone type or other potassium-containing compounds (salts or the like) which replenish $K^+$ losses.

EXAMPLE 1

4-(4-Methylphenoxy)-3-(2,5-dimethyl-1-pyrrolidinyl)-5-sulfamoyl-benzoic acid (a) Methyl 3-N-(2,5-dimethylpyrrolo)-4-(4-methylphenoxy)-5-N,N-dimethylaminomethyleneaminosulfonyl-benzoate 25 g (0.064 mole) of methyl 3-amino-4-(4-methylphenoxy)-5-N,N-dimethylaminomethyleneaminosulfonyl-benzoate in 250 ml of glacial acetic acid and 20 ml (0.168 mole) of acetonylacetone are heated under reflux for 1 hour. The solution is stirred into ice-water and the product which has precipitated is recrystallized from methanol.

White crystals with a melting point of 190°-192° C.

(b) 3-N-(2,5-Dimethylpyrrolo)-4-(4-methylphenoxy)-5-sulfamoyl-benzoic acid 22 g (0.047 mole) of methyl 3-N-(2,5-dimethylpyrrolo)-4-(4-methylphenoxy)-5-N,N-dimethylaminomethyleneaminosulfonylbenzoate are suspended in 250 ml of 2N NaOH and the suspension is heated under reflux until a clear solution is obtained. Neutralizing the solution with 2N HCl allows the free acid to precipitate. Recrystallization from ether/petroleum ether. Melting point 207°–210° C.

(c) 4-(4-Methylphenoxy)-3-(2,5-dimethyl-1-pyrrolidinyl)-5-sulfamoyl-benzoic acid 10 g (0.025 mole) of 3-N-(2,5-dimethylpyrrolo)-4-(4-methylphenoxy)-5-sulfamoyl-benzoic acid are dissolved in 200 ml of methanol, 7 g of 10% strength palladium-on-charcoal are added and the mixture is hydrogenated for 12 hours at 70° C. under 100 atmospheres. The solution is filtered, the filtrate is concentrated and water is added. The product crystallizes out. White crystals with a melting point of 191°–193° C.

EXAMPLE 2

4-(4-Methylphenoxy)-3-(2-methyl-1-pyrrolidinyl)-5-sulfamoyl-benzoic (a) Methyl 3-N-(2-methylpyrrolo)-4-(4-methylphenoxy)-5-N,N'-dimethylaminomethyleneaminosulfonyl-benzoate 10 g (0.026 mole) of methyl 3-amino-4-(4-methylphenoxy)-5-N,N'-dimethylaminomethyleneaminosulfonyl-benzoate are dissolved in a mixture of 50 ml of methylene chloride and 50 ml of glacial acetic acid, and 7 ml (0.048 mole) of 2,5-dimethoxy-2-methyltetrahydrofuran are added. The mixture is stirred at room temperature for one hour and water is then added. The $CH_2Cl_2$ phase is washed repeatedly with water, dried over $Na_2SO_4$ and concentrated. The product crystallizes out on the addition of ether.

White crystals with a melting point of 215° C.

(b) 3-N-(2-Methylpyrrolo)-4-(4-methylphenoxy)-5-sulfamoyl-benzoic acid 11.1 g (0.024 mole) of methyl 3-N-(2-methylpyrrolo)-4-(4-methylphenoxy)-5-N,N-dimethylaminomethyleneaminosulfonylbenzoate are suspended in 150 ml of 2N NaOH and the suspension is heated under reflux until a clear solution is obtained. Acidifying with 2N HCl allows the free acid to precipitate. Recrystallization from methanol/water.

Melting point 217°–219° C.

(c) 4-(4-Methylphenoxy)-3-(2-methyl-1-pyrrolidinyl)-5-sulfamoyl-benzoic acid 8.2 g (0.024 mole) of 3-N-(2-methylpyrrolo)-4-(4-methylphenoxy)-5-sulfamoyl-benzoic acid are dissolved in 150 ml of methanol, 4 g of 10% strength palladium-on-charcoal are added and the mixture is hydrogenated for 10 hours at 70° C. and under 100 atmospheres. The solution is filtered, the filtrate is evaporated to dryness and the residue is recrystallized from methanol/water.

White crystals with a melting point of 234°–236° C.

EXAMPLE 3

4-Phenoxy-3-(2-methyl-1-pyrrolidinyl)-5-sulfamoylbenzoic acid (a) Methyl 3-N-(2-methylpyrrolo)-4-phenoxy-5-N,N-dimethylaminomethyleneaminosulfonyl-benzoate 12.2 g (0.032 mole) of methyl 3-amino-4-phenoxy-5-N,N-dimethylaminomethyleneaminosulfonyl-benzoate in 150 ml of glacial acetic acid are heated to the reflux temperature and 7 ml (0.048 mole) of 2,5-dimethoxy-2-methyl-tetrahydrofuran are added. After a reaction time of 15 minutes, the mixture is stirred into ice-water and the product which has precipitated is recrystallized from methanol.

Melting point: 188°–189° C.

(b) 3-N-(2-Methylpyrrolo)-4-phenoxy-5-sulfamoyl-benzoic acid 10 g (0.023 mole) of methyl 3-N-(2-methylpyrrolo)-4-phenoxy-5-N,N-dimethylaminomethyleneaminosulfonyl-benzoate are suspended in 150 ml of 2N NaOH and the suspension is heated under reflux until a clear solution is obtained. On acidifying with 2N HCl, the free acid is obtained. Recrystallization from methanol.

Melting point: 265°–266° C.

(c) 4-Phenoxy-3-(2-methyl-1-pyrrolidinyl)-5-sulfamoylbenzoic acid 13 g (0.35 mole) of 3-N-(2-methylpyrrolo)-4-phenoxy-5-sulfamoylbenzoic acid are dissolved in 200 ml of methanol, 1 g of 10% strength palladium-on-charcoal is added and the mixture is hydrogenated for 8 hours at 100° C. and under 100 atmospheres. The solution is filtered and the solvent is stripped off. The residue is recrystallized from methanol/water.

White crystals with a melting point of 221°–223° C.

EXAMPLE 4

4-Phenoxy-3-(2,5-dimethyl-1-pyrrolidinyl)-5-sulfamoylbenzoic acid (a) Methyl 3-N-(2,5-dimethylpyrrolo)-4-phenoxy-5-N,N-dimethylaminomethyleneaminosulfonyl-benzoate 25 g (0.067 mole) of methyl 3-amino-4-phenoxy-5-N,N-dimethylaminomethyleneaminosulfonyl-benzoate in 150 ml of glacial acetic acid are heated to the boil and 17 ml (0.116 mole) of acetonylacetone are added. After a reaction time of 30 minutes, the mixture is stirred into ice-water and the product which has precipitated is filtered off. Recrystallization from methanol.

Melting point: 198° C.

(b) 3-N-(2,5-Dimethylpyrrolo)-4-phenoxy-5-sulfamoylbenzoic acid 10 g (0.022 mole) of methyl 3-N-(2,5-dimethylpyrrolo)-4-phenoxy-5-N,N-dimethylaminomethyleneaminosulfonyl-benzoate are saponified analogously to Example 3b. Recrystallization from methanol. Melting point: 280°–292° C. (decomposition).

(c) 4-Phenoxy-3-(2,5-dimethyl-1-pyrrolidinyl)-5-sulfamoylbenzoic acid 14.5 g (0.038 mole) of 3-N-(2,5-dimethylpyrrolo)-4-phenoxy-5-sulfamoylbenzoic acid are dissolved in 200 ml of methanol, 1 g of 10% strength palladium-on-charcoal is added and the mixture is hydrogenated for 8 hours at 100° C. and under 100 atmospheres. The mixture is filtered, the filtrate is freed from the solvent and the residue is recrystallized from methanol/water.

Melting point: 207°–210° C. (decomposition).

EXAMPLE 5

4-(4-Methylphenoxy)-3-(2-ethyl-5-methyl-1-pyrrolidinyl)-5-sulfamoylbenzoic acid (a) Methyl 3-N-(2-ethyl-5-methylpyrrolo)-4-(4-methylphenoxy)-5-N,N-dimethyl-aminomethyleneaminosulfonyl-benzoate 10 g (0.026 mole) of methyl 3-amino-4-(4-methylphenoxy)-5-N,N-dimethylaminomethyleneaminosulfonyl-benzoate are dissolved in 60 ml of dioxane, and 50 mg of p-toluenesulfonic acid and 10 ml (0.076 mole) of heptane-2,5-dione are added. The mixture is heated under reflux for 2 hours and stirred into ice-water. The product which has precipitated is recrystallized from methanol.

Melting point: 192°–195° C.

(b) 3-N-(2-Ethyl-5-methylpyrrolo)-4-(4-methylphenoxy)-5-sulfamoyl-benzoic acid 9.1 g (0.019 mole) of methyl 3-N-(2-ethyl-5-methylpyrrolo)-4-(4-methylphenoxy)-5-N,N-dimethylaminomethyleneaminosulfonyl-benzoate are suspended in 100 ml of 2N NaOH and the suspension is heated under reflux until a clear solution is obtained. On acidifying to pH 1–2, the free acid precipitates. Recrystallization from methanol/$H_2O$.

Melting point: 228°–231° C.

(c) 4-(4-Methylphenoxy)-3-(2-ethyl-5-methyl-1-pyrrolidinyl)-5-sulfamoylbenzoic acid 3.2 g (0.008 mole) of 3-N-(2-ethyl-5-methylpyrrolo)-4-(4-methyl-phenoxy)-5-sulfamoylbenzoic acid are dissolved in 100 ml of methanol and, with the addition of 1.7 g of 10% strength palladium-on-charcoal, hydrogenated at room temperature and under 100 atmospheres. The catalyst is filtered off, the filtrate is concentrated to dryness and petroleum ether 40–60/a little toluene is added to the residue. The product crystallizes.

Recrystallization from methanol/$H_2O$. Melting point: 198°–200° C.

EXAMPLE 6

4-(4-Methoxyphenoxy)-3-(2,5-dimethyl-1-pyrrolidinyl)-5-sulfamoylbenzoic acid (a) Methyl 3-N-(2,5-dimethylpyrrolo)-4-(4-methoxyphenoxy)-5-N,N-dimethylaminomethyleneaminosulfonyl-benzoate 20.0 g (0.049 mole) of methyl 3-amino-4-(4-methylphenoxy)-5-N,N-dimethylaminomethyleneaminosulfonyl-benzoate and 12 ml (0.1 mole) of acetonylacetone in 200 ml of glacial acetic acid are heated under reflux. After a reaction time of 45 minutes, the mixture is stirred into ice-water. The product which has precipitated is recrystallized from methylene chloride/diethyl ether.

Colorless crystals with a melting point of 214°–216° C.

(b) 3-N-(2,5-Dimethylpyrrolo)-4-(4-methoxyphenoxy)-5-sulfamoylbenzoic acid 5 g (0.010 mole) of methyl 3-N-(2,5-dimethylpyrrolo)-4-(4-methoxyphenoxy)-5-N,N-dimethylaminomethyleneaminosulfonyl-benzoate are suspended in 50 ml of 2N NaOH and the suspension is heated under reflux until a clear solution is obtained. On acidifying with 2N HCl to pH 5–6, the free acid precipitates. Recrystallization from $CH_3OH/H_2O$.

White crystals with a melting point of 207°–209° C.

(c) 4-(4-Methoxyphenoxy)-3-(2,5-dimethyl-1-pyrrolidinyl)-5-sulfamoylbenzoic acid 3.8 g (0.009 mole) of 3-N-(2,5-dimethylpyrrolo)-4-(4-methoxyphenoxy)-5-sulfamoylbenzoic acid are dissolved in 50 ml of methanol and hydrogenated for 8 hours at 100° C. and under 100 atmospheres, with the addition of 500 mg of 10% strength palladium/active charcoal. The catalyst is filtered off and the solution is concentrated in a rotary evaporator until it starts it crystallize.

Pink-tinged crystals with a melting point of 179°–181° C.

EXAMPLE 7

4-(4-Methylphenoxy)-3-(2-ethyl-1-pyrrolidinyl)-5-sulfamoylbenzoic acid (a) Methyl 3-N-(2-ethylpyrrolo)-4-(4-methylphenoxy)-5-N,N-dimethylaminomethyleneaminosulfonyl-benzoate 10 g (0.026 mole) of 3-amino-4-(4-methylphenoxy)-5-N,N-dimethylaminomethyleneaminosulfonyl-benzoic acid are dissolved in a mixture of 75 ml of glacial acetic acid and 75 ml of methylene chloride. The solution is heated under reflux for 30 minutes and, during this time, 8 ml (0.05 mole) of 2,5-dimethoxy-2-ethyl-tetrahydrofuran are added dropwise. After boiling under reflux for a further 10 minutes, the solution is washed with water and concentrated and diethyl ether is added. The product crystallizes out.

White crystals with a melting point of 193°–195° C.

(b) 3-N-(2-Ethylpyrrolo)-4-(4-methylphenoxy)-5-sulfamoylbenzoic acid 12 g (0.026 mole) of methyl 3-N-(2-ethylpyrrolo)-4-(4-methylphenoxy)-5-N,N-dimethylaminomethyleneaminosulfonyl-benzoate are suspended in 150 ml of 2N NaOH and the suspension is heated until a clear solution is obtained. The product is precipitated by acidifying with 2N HCl to pH 5–6. Recrystallization from methanol/$H_2O$.

Melting point: 236°–237° C.

(c) 4-(4-Methylphenoxy)-3-(2-ethyl-1-pyrrolidinyl)-5-sulfamoylbenzoic acid 6.2 g (0.015 mole) of 3-N-(2-ethylpyrrolo)-4-(4-methylphenoxy)-5-sulfamoylbenzoic acid are dissolved in 100 ml of methanol and, with the addition of 3 g of 10% strength palladium-on-charcoal, hydrogenated for 14 hours at 70° C. and under 100 atmospheres. The solution is filtered, the filtrate is concentrated to dryness and the residue is recrystallized from methanol/$H_2O$.

Melting point: 235°–237° C.

EXAMPLE 8

4-(4-Methylanilino)-3-(2,5-dimethyl-1-pyrrolidinyl)-5-sulfamoylbenzoic acid (a) Methyl 3-N-(2,5-dimethylpyrrolo)-4-(4-methylanilino)-5-N,N-dimethylaminomethyleneaminosulfonyl-benzoate 20 g (0.051 mole) of methyl 3-amino-4-(4-methylanilino)-5-N,N-dimethylaminomethyleneaminosulfonyl-benzoate are dissolved in 150 ml of glacial acetic acid, 15 ml (0.126 mole) of acetonylacetone are added and the mixture is heated under reflux for 20 minutes. The mixture is stirred into ice-water and the product which has precipitated is recrystallized from methanol/$H_2O$. Colorless crystals with a melting point of 178°–180° C.

(b) 3-N-(2,5-Dimethylpyrrolo)-4-(4-methylanilino)-5-sulfamoylbenzoic acid 12.0 g (0.026 mole) of methyl 3-N-(2,5-dimethylpyrrolo)-4-(4-methylanilino)-5-N,N-dimethylaminomethyleneaminosulfonyl-benzoate in 150 ml of 2N NaOH are heated under reflux until a clear solution is obtained. Acidifying with 2N HCl allows the free acid to precipitate. Recrystallization from methanol/$H_2O$.

Melting point: 212°–214° C.

(c) 4-(4-Methylanilino)-3-(2,5-dimethyl-1-pyrrolidinyl)-5-sulfamoylbenzoic acid 5.4 g (0.014 mole) of 3-N-(2,5-dimethylpyrrolo)-4-(4-methylanilino)-5-sulfamoylbenzoic acid are dissolved in 100 ml of methanol, 3 g of 10% strength palladium-on-charcoal are added and the mixture is hydrogenated for 16 hours at 60° C. and under 150 atmospheres. After filtering and stripping off the solvent, the residue is recrystallized from toluene.

Melting point: 212°–214° C.

EXAMPLE 9

4-(4-Methoxyphenoxy)-3-(2-methyl-1-pyrrolidinyl)-5-sulfamoylbenzoic acid (a) Methyl 3-N-(2-methylpyrrolo)-4-(4-methoxyphenoxy)-5-N,N-dimethylaminomethyleneaminosulfonyl-benzoate 8 g (0.020 mole) of methyl 3-amino-4-(4-methoxyphenoxy)-5-N,N-dimethylaminomethyleneaminosulfonyl-benzoate are dissolved in a mixture of 60 ml of methylene chloride and 60 ml of glacial acetic acid, 6 ml (0.04 mole) of 2,5-dimethoxy-2-methyltetrahydrofuran are added and the mixture is stirred for 60 minutes at room temperature. The glacial acetic acid is separated off by washing repeatedly with water, the methylene chloride is stripped off and the residue is recrystallized from ether/a little methylene chloride.

Melting point: 191°–192° C.

(b) 3-N-(2-Methylpyrrolo)-4-(4-methoxyphenoxy)-5-sulfamoylbenzoic acid 7.5 g (0.016 mole) of methyl 3-N-(2-methylpyrrolo)-4-(4-methoxyphenoxy)-5-N,N-dimethylaminomethyleneaminosulfonyl-benzoate are suspended in 100 ml of 2N NaOH and the suspension is heated under reflux until a clear solution is obtained. Acidifying to pH 3–4 allows the free acid to precipitate. Recrystallization from methanol/water.

Melting point: 193°–195° C.

(c) 4-(4-Methoxyphenoxy)-3-(2-methyl-1-pyrrolidinyl)-5-sulfamoylbenzoic acid 3.2 g (0.009 mole) of 3-N-(2-methylpyrrolo)-4-(4-methoxyphenoxy)-5-sulfamoylbenzoic acid are dissolved in 50 ml of glacial acetic acid, 1 g of 10% strength palladium-on-charcoal is added and the mixture is hydrogenated for 10 hours at 80° C. and under 20 atmospheres. After filtering, the filtrate is stirred into water. The product crystallizes out.

Melting point: 197°–199° C.

EXAMPLE 10

4-(2-Thienyl)-3-(2,5-dimethyl-1-pyrrolidinyl)-5-sulfamoylbenzoic acid (a) Methyl 3-N-(2,5-dimethylpyrrolo)-4-(2-thienyl)-5-N,N-dimethylaminomethyleneaminosulfonylbenzoate 18.4 g (0.05 mole) of methyl 3-amino-4-(2-thienyl)-5-N,N-dimethylaminomethyleneaminosulfonylbenzoate are dissolved in 150 ml of glacial acetic acid, 6.3 g (0.055 mole) of acetonylacetone are added and the mixture is heated under reflux for 60 minutes. It is poured into ice-water and the product is filtered off. Recrystallization from ethanol with the addition of animal charcoal.

Melting point: 205°–207° C.

(b) Methyl 3-N-(2,5-dimethyl-1-pyrrolidinyl)-4-(2-thienyl)-5-N,N-dimethylaminomethyleneaminosulfonylbenzoate 10 g of "pyrrole ester" (10 a) are dissolved in 250 ml of glacial acetic acid, 7.5 g of 10% strength palladium-on-charcoal are added and the mixture is hydrogenated for 15 hours at 80° C. and under 100 atmospheres. The solution is filtered, the filtrate is concentrated to 100 ml, 500 ml of ice-water are added and the mixture is filtered again. The solution is extracted several times with ethyl acetate and the combined ethyl acetate extracts are dried over magnesium sulfate and concentrated to dryness. Recrystallization from isopropanol.

Crystals with a melting point of 180°–182° C.

(c) 4-(2-Thienyl)-3-(2,5-dimethylpyrrolidinyl)-5-sulfamoylbenzoic acid 2.25 g (0.005 mole) of "pyrrolidine ester" (10 b) are suspended in 2N NaOH and the suspension is heated under reflux until a clear solution is obtained. Acidifying with 2N HCl to pH 1 allows the free acid to precipitate.

Crystals with a melting point of 220°–222° C.

EXAMPLE 11

4-(3-Pyridyloxy)-3-(2,5-dimethyl-1-pyrrolidinyl)-5-sulfamoylbenzoic acid (a) Methyl 5-dimethylaminomethyleneaminosulfonyl-3-nitro-4-(3-pyridyloxy)-benzoate A solution of 200 g (0.57 mole) of methyl 4-chloro-5-dimethylaminomethyleneaminosulfonyl-3-nitro-benzoate and 93 g (0.7 mole) of potassium 3-hydroxypyridine in 1 l of dimethylformamide is stirred for 1.5 hours at 80° C. and, after cooling, is introduced into 4–5 l of ice-water, while stirring vigorously. The product which has precipitated is filtered off, washed with $H_2O$ and recrystallized from dimethylformamide/$CH_3OH$.

Crystals with a melting point of 171°–173° C.

(b) Methyl 3-amino-5-dimethylaminomethyleneaminosulfonyl-4-(3-pyridyloxy)-benzoate 150 g of methyl 5-dimethylaminomethyleneaminosulfonyl-3-nitro-4-(3-pyridyloxy)-benzoate are hydrogenated in dimethylformamide at 50° C. and under 50 atmospheres for 15 hours in an autoclave, using Raney nickel as the catalyst. The reaction mixture is then filtered, the filtrate is concentrated and the residue is recrystallized from dimethylformamide/$CH_3OH$.

Crystals with a melting point of 234°.

(c) Methyl 3-N-(2,5-dimethylpyrrolo)-4-(3-pyridyloxy)-5-N,N-dimethylaminomethyleneaminosulfonyl-benzoate 19 ml (0.16 mole) of acetonylacetone are added to 20 g (0.053 mole) of methyl 3-amino-5-dimethylaminomethyleneaminosulfonyl-4-(3-pyridyloxy)-benzoate in 200 ml of glacial acetic acid, at the boiling point. After two hours under reflux (monitoring by means of thin layer chromatography), the resulting solution is introduced into ice-water. On the addition of 5–10 ml of 2N NaOH, a violet colored precipitate separates. The crude product is boiled thoroughly with methanol and recrystallized from acetone. Cream colored crystals with a melting point of 219°–220° C.

(d) 3-N-(2,5-Dimethyl-pyrrolo)-4-(3-pyridyloxy)-5-sulfamoylbenzoic acid 15.3 g of the ester obtained in (11 c) are suspended in 1N NaOH and the suspension is heated under reflux until a clear solution is obtained (30–40 minutes). The free acid is then precipitated in the cold.

Crystals with a melting point of 293°–294°.

(e) 4-(3-Pyridyloxy)-3-(2,5-dimethyl-1-pyrrolidinyl)-5-sulfamoylbenzoic acid 12 g of 3-N-(2,5-dimethyl-pyrrolo)-4-(3-pyridyloxy)-5-sulfamoyl-benzoic acid in 240 ml of glacial acetic acid are hydrogenated with 3 g of Pd/C (10%) at 100° and with hydrogen under 20 atmospheres, for 12 hours in an autoclave. The reaction mixture is then filtered, the filtrate is concentrated and the residue is recrystallized from CH₃OH/H₂O.

Crystals with a melting point of 247°–248° C.

EXAMPLE 12

4-(3-Pyridyloxy)-3-(2-methyl-1-pyrrolidinyl)-5-sulfamoylbenzoic acid (a) Methyl 3-N-(2-methylpyrrol)-4-(3-pyridyloxy)-5-N,N-dimethylaminomethyleneaminosulfonylbenzoate 15 ml (0.102 mole) of 2,5-dimethoxy-2-methyltetrahydrofurane are added to 20 g (0.052 mole) of methyl 3-amino-5-dimethylaminomethyleneaminosulfonyl-4-(3-pyridyloxy)-benzoate in a solution of 100 ml of glacial acetic acid and 100 ml of methylene chloride, at the boiling point. After boiling under reflux for 10 minutes, the mixture is cooled (monitoring by means of thin layer chromatography) and introduced into 500 ml of ice-water. The methylene chloride layer is separated, the aqueous solution is extracted once more with 100 ml of methylene chloride and the combined, dried methylene chloride extracts are evaporated and the residue is triturated with ether. Crystals with a melting point of 194°–196° C.

(b) 3-N-(2-Methylpyrrolo)-4-(3-pyridyloxy)-5-sulfamoylbenzoic acid 11.6 g of the ester obtained in (12 a) are suspended in 1N NaOH and the suspension is heated under reflux until a clear solution is obtained. After cooling and filtering the solution, the free acid is precipitated with 4N HCl (pH 2–3).

Crystals with a melting point of 284°–285° C.

(c) 4-(3-Pyridyloxy)-3-(2-methyl-1-pyrrolidinyl)-5-sulfamoylbenzoic acid

Prepared analogously to Example 11 e.

Crystals with a melting point of 264°–265° C.

EXAMPLE 13

4-(6-Methyl-3-pyridyloxy)-3-(2,5-dimethyl-1-pyrrolidinyl)-5-sulfamoylbenzoic acid (a) Methyl 5-dimethylaminomethyleneaminosulfonyl-4-(6-methyl-3-pyridyloxy)-3-nitro-benzoate Prepared analogously to Example 11a, using the potassium salt of 3-hydroxy-6-methylpyridine.

Pale yellow crystals from dimethylformamide/CH₃OH, with a melting point of 149°–150° C.

(b) Methyl 3-amino-5-dimethylaminomethyleneaminosulfonyl-4-(6-methyl-3-pyridyloxy)-benzoate Prepared analogously to Example 11b.

Recrystallization from methanol. Melting point: 150°.

(c) Methyl 3-N-(2,5-dimethylpyrrolo)-4-(6-methyl-3-pyridyloxy)-5-N,N-dimethylaminomethyleneaminosulfonyl)-benzoate 26 ml (0.23 mole) of acetonylacetone are added dropwise to 29.6 g (0.075 mole) of "amine ester" (13b) in 300 ml of glacial acetic acid, at the boiling point. After stirring for 1½ hours under reflux, the reaction mixture is introduced into 1 l of ice-water. After adding 2N NaOH, a precipitate separates on standing overnight in a refrigerator.

Crystals with a melting point of 212°–213° C.

(d) 3-N-(2,5-Dimethylpyrrolo)-4-(6-methyl-3-pyridyloxy)-5-sulfamoyl-benzoic acid 20 g of the ester obtained in 13c in 150 ml of 2N NaOH are heated under reflux until a clear solution is obtained and the free acid is precipitated in the cold with 4N HCl. Crystals with a melting point of 292°–293° C. (from CH₃OH/H₂O).

(e) 4-(6-Methyl-3-pyridyloxy)-3-(2,5-dimethyl-1-pyrrolidinyl)-5-sulfamoylbenzoic acid 10 g of the compound prepared under 13d are hydrogenated in 150 ml of glacial acetic acid in the presence of 3 g of Pd/C (10%) at 100° and with hydrogen under 20 atmospheres, for 15 hours in an autoclave. After filtering, the filtrate is concentrated and the residue is recrystallized from CH₃OH/H₂O.

Crystals with a melting point of 246°–247° C.

EXAMPLE 14

4-(6-Methyl-3-pyridyloxy)-3-(2-methyl-1-pyrrolidinyl)-5-sulfamoylbenzoic acid (a) 3-N-(2-Methylpyrrolo)-4-(6-methyl-3-pyridyloxy)-5-sulfamoylbenzoic acid 15 ml (0.1 mole) of 2,5-dimethoxy-2-methyltetrahydrofurane are added to 19.6 g (0.05 mole) of methyl 3-amino-5-dimethylaminomethyleneaminosulfonyl-4-(6-methyl-3-pyridyloxy)-benzoate in a solution of 100 ml of glacial acetic acid and 100 ml of methylene chloride, at the boiling point. After boiling under reflux for 10 minutes, the reaction mixture is cooled and introduced into 500 ml of ice-water. The methylene chloride layer is separated, the aqueous solution is extracted once more with 100 ml of methylene chloride and the combined, dried methylene chloride extracts are evaporated. The residue is triturated with ether, filtered off and suspended in 2N NaOH and the suspension is heated under reflux until a clear solution is obtained. After cooling and filtering the solution, the free acid is precipitated with 4N HCl. Crystals with a melting point of 176°–178° C. (from CH₃OH/H₂O).

(b) 4-(6-Methyl-3-pyridyloxy)-3-(2-methyl-1-pyrrolidinyl)-5-sulfamoylbenzoic acid 18 g of 3-N-(2-methylpyrrolo)-4-(6-methyl-3-pyridyloxy)-5-sulfamoyl-benzoic acid are hydrogenated in 350 ml of glacial acetic acid with 6 g of Pd/C (10%) at 100° and with hydrogen under 20 atmospheres, for 15 hours in an autoclave. After filtering, the filtrate is concentrated and the residue is recrystallized from CH₃OH/H₂O.

Crystals with a melting point of 235°–254° C.

EXAMPLE 15

4-(4-Methylphenyl)-3N-(2,5-dimethyl-pyrrolo)-5-sulfamoylbenzoic acid (a) Methyl 4-(4-methylphenyl-3-nitro-5-dimethylaminomethyleneaminosulfonyl-benzoate A mixture of 50 g (0.14 mole) of methyl 4-chloro-3-nitro-5-dimethylaminomethyleneaminosulfonyl-benzoate, 70 g (0.51 mole) of 4-bromotoluene and 42.8 g (0.68 mole) of Cu powder is stirred under nitrogen for 6 hours at 170°–175° C.; it is then cooled to 100° C. and diluted with 200 ml of dimethylformamide and insoluble copper salts are filtered off and washed with 200 ml of dimethylformamide. The crude product is precipitated from the combined, concentrated dimethylformamide solutions by adding 250 ml of methanol.

Crystals with a melting point of 170°–173° C. (from dimethylformamide/CH₃OH).

(b) Methyl 3-amino-4-(4-methylphenyl)-5-dimethylaminomethyleneaminosulfonyl-benzoate A solution of 28 g (0.07 mole) of methyl 4-(4-methylphenyl)-3-nitro-5-dimethylaminomethyleneaminosulfonyl-benzoate in 200 ml of dimethylformamide is hydrogenated with 3 g of Raney nickel at 50° and with hydrogen under a pressure of 50 atmospheres, for 10 hours in an autoclave. After filtering, the filtrate is introduced into ice-water and the precipitate is filtered off and recrystallized from dimethylformamide/MeOH.

Crystals with a melting point of 225° C.

(c) Methyl 4-(4-methylphenyl)-3N-(2,5-dimethyl-pyrrolo)-5-dimethylaminomethyleneaminosulfonyl-benzoate 5 g of acetonylacetone are added dropwise to a solution of 15 g (0.04 mole) of methyl 3-amino-4-(4-methylphenyl)-5-dimethylaminomethyleneaminosulfonyl-benzoate in 100 ml of glacial acetic acid, at the boiling point. After stirring under reflux for one hour (monitoring by means of thin layer chromatography), the resulting solution is introduced into ice-water. The precipitate is filtered off and washed with water.

Crystals with a melting point of 225°–228° C.

(d) 4-(4-Methylphenyl)-3N-(2,5-dimethylpyrrolo)-5-sulfamoylbenzoic acid 6 g of the ester obtained in 15 c are suspended in 1N NaOH and the suspension is heated under reflux until a clear solution is obtained. The free acid is precipitated with 2N HCl, with ice-cooling.

Crystals with a melting point of 280°–283° C.

We claim:

1. A substituted pyrrolidinylsulfamoylbenzoic acid compound of the formula

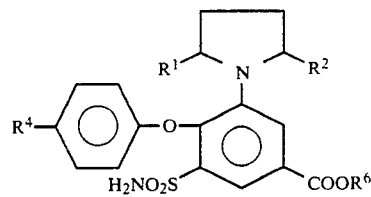

or a pharmaceutically acceptable salt thereof with an acid or a base, wherein $R^1$ and $R^2$ are the same or different and are both methyl having 1 to 4 carbon atoms or wherein one of $R^1$ or $R^2$ is hydrogen and the other is such methyl;

$R^4$ is methyl or ethyl; and $R^6$ is hydrogen or alkyl having 1 to 4 carbon atoms.

2. A compound as in claim 1 which is 4-(4-methylphenoxy)-3-(2-methyl-1-pyrrolidinyl)-5-sulfamoyl benzoic acid.

3. A compound as in claim 1 which is 4-(4-methylphenoxy)-3-(2,5-dimethyl-1-pyrrolidinyl)-5-sulfamoyl benzoic acid.

4. A compound as in claim 1 which is 4-(4-ethylphenoxy)-3-(2-methyl-1-pyrrolidinyl)-5-sulfamoyl benzoic acid.

5. A saluretic and diuretic pharmaceutical composition comprising a saluretically- and diuretically-effective amount of a compound or salt as in claim 1 and a pharmaceutically acceptable carrier therefor.

6. A method of treatment which comprises administering to a patient a diuretically and saluretically effective amount of a compound or salt as in claim 1.

7. A compound or salt as in claim 1 wherein $R^4$ is hydrogen or methyl.

* * * * *

UNITED STATES PATENT AND TRADEMARK OFFICE
CERTIFICATE OF CORRECTION

PATENT NO. : 4,492,710

DATED : January 8, 1985

INVENTOR(S) : Wulf Merkel, Dieter Bormann and Roman Muschaweck

It is certified that error appears in the above-identified patent and that said Letters Patent is hereby corrected as shown below:

Claim 1, line 5 (Col. 14, line 4) delete "the same or different and are";
line 6 (Col. 14, line 5) delete "having 1 to 4 carbon atoms"; and
line 7 (Col. 14, line 6) delete "such".

Signed and Sealed this

Fifteenth Day of October 1985

[SEAL]

Attest:

Attesting Officer

DONALD J. QUIGG

*Commissioner of Patents and Trademarks—Designate*